United States Patent [19]

Bender et al.

[11] 4,258,043

[45] Mar. 24, 1981

[54] PYRAZINO-CARBAZOLES, PROCESS FOR THE PRODUCTION THEREOF AND PHARMACEUTICAL AGENTS

[75] Inventors: Heinz Bender; Rudi Beyerle, both of Frankfurt am Main; Steffen Piesch, Oberursel; Piero A. Martorana, Bad Homburg von der Hohe, all of Fed. Rep. of Germany

[73] Assignee: Cassella Aktiengesellschaft, Frankfurt am Main-Fechenheim, Fed. Rep. of Germany

[21] Appl. No.: 98,608

[22] Filed: Nov. 29, 1979

[51] Int. Cl.³ .................. A61K 31/495; C07D 209/88; C07D 493/16

[52] U.S. Cl. .................................... 424/250; 260/315; 544/343

[58] Field of Search ........................ 544/343; 260/315; 424/250

[56] References Cited

FOREIGN PATENT DOCUMENTS 255278  3/1970  U.S.S.R. .................................. 544/343

OTHER PUBLICATIONS

Mashkovskii et al., Chem. Abs., vol 78 (1973) 124624w.
Gatta et al., Chem. Abs., vol. 83 (1975) 131553w.

*Primary Examiner*—Paul M. Coughlan, Jr.
*Attorney, Agent, or Firm*—Berman, Aisenberg & Platt

[57] ABSTRACT

The present invention relates to new, pharmacologically-valuable antidepressants, which are 2,4,5,6-tetrahydro-1H-pyrazino-[3,2,1-jk]-carbazoles substituted in the 8-position and having the formula I

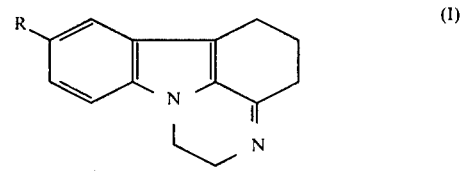

(I)

wherein R stands for an alkyl or alkoxy group having 1 to 4 carbon atoms or a fluorine, chlorine or bromine atom, and a method for making them by reacting with ammonia a 6,9-disubstituted 1,2,3,4-tetrahydrocarbazol-1-one of the formula II

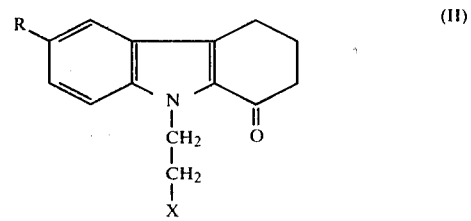

(II)

wherein X denotes a bromine, chlorine or iodine atom or a radical of the formula $-O-SO_2-R'$, and $R'$ is an alkyl radical having 1 to 3 carbon atoms, phenyl or tolyl.

11 Claims, No Drawings

PYRAZINO-CARBAZOLES, PROCESS FOR THE PRODUCTION THEREOF AND PHARMACEUTICAL AGENTS

The present invention relates to pharmacologically valuable 2,4,5,6-tetrahydro-1H-pyrazino-[3,2,1-jk]-carbazoles substituted in the 8-position having the formula I

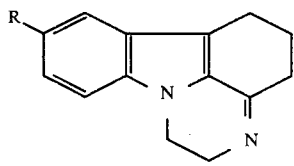

wherein R stands for an alkyl or alkoxy group having 1 to 4 carbon atoms or a fluorine, chlorine or bromine atom as well as the acid addition salts thereof, their production and the pharmaceutically acceptable psychotropic agents which contain the same.

Suited for the formation of the pharmaceutically acceptable acid addition salts of the compounds of the general formula I are inorganic and organic acids, for instance: hydrogen chloride, hydrogen bromide, naphthalene disulfonic acid (1,5), phosphoric acid, nitric acid, sulfuric acid, oxalic acid, lactic acid, tartaric acid, acetic acid, salicylic acid, benzoic acid, formic acid, propionic acid, pivalic acid, diethyl acetic acid, malonic acid, succinic acid, pimelic acid, furmaric acid, maleic acid, malic acid, sulfamic acid, phenylpropionic acid, gluconic acid, ascorbic acid, isonicotinic acid, methanesulfonic acid, p-toluene sulfonic acid, citric or adipic acid.

The acid addition salts may be obtained in the conventional fashion by combining the components, for the sake of expediency, in a suitable diluent or dispersant.

The compounds of formula I are obtained by reacting a 6,9-disubstituted 1,2,3,4-tetrahydrocarbazol-1-one of the formula II

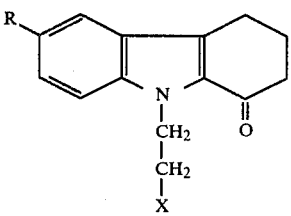

with ammonia by cyclisation wherein R stands for an alkyl or alkoxy group having 1 to 4 carbon atoms or a fluorine, chlorine or bromine atom and X denotes a bromine, chlorine or iodine atom or the radical of the formula —O—SO$_2$—R', and R' represents alkyl radical having 1 to 3 carbon atoms, phenyl or tolyl.

The new 2,6-disubstituted 1,2,3,4-tetrahydrocarbonzol-1-ones of the formula IIa which are employed as starting compounds are obtained by reacting 1,2,3,4-tetrahydrocarbazol-1-ones of the formula III (which are substituted in the 6-position) with 1,2-dihalogenethanes or the sulfonic acid esters of 1-hydroxy-2-halogenethanes:

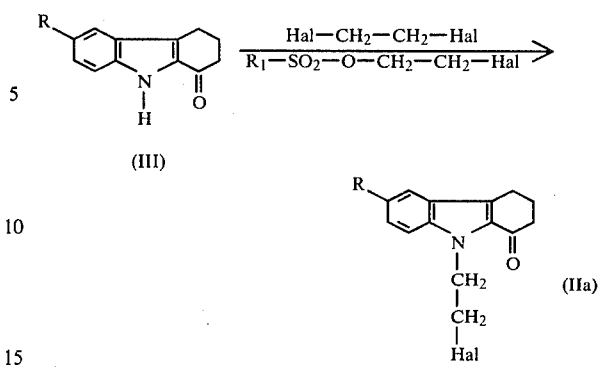

In this instance Hal stands for chlorine, bromine or iodine and R$_1$ for alkyl, aryl or aralkyl. Suitable 1,2-dihalogenethanes and sulfonic acid esters of 1-hydroxy-2-halogenethanes are, accordingly, those which contain as halogen, chlorine, bromine or iodine, for instance 1,2-dichloroethane, 1,2-dibromoethane or 1,2-diiodoethane. 1,2-dihalogenethanes, too, containing two different halogen atoms, such as 1-bromo-2-chloroethane, are suitable. In the sulfonic acid esters of the 1-hydroxy-2-bromoethane, 1-hydroxy-2-chloroethane or 1-hydroxy-2-iodoethane the sulfonic acid ester group can be derived from an alkyl sulfonic acid, especially from one having 1 to 4 carbon atoms, for instance methanesulfonic acid, ethanesulfonic acid or n-butanesulfonic acid, from an arenesulfonic acid, especially with 6 to 12 carbon atoms, for example benzenesulfonic acid, ortho toluene sulfonic acid, meta or para toluene sulfonic acid or 2,3-xylene sulfonic acid, 2,4-xylene sulfonic acid or 3,5-xylene sulfonic acid or α- or β-naphthalene sulfonic acid, from an arylalkanesulfonic acid, particularly having 7 or 8 carbon atoms, such as phenylmethane sulfonic acid or phenylethane sulfonic acid.

The reaction of the tetrahydrocarbazolones of formula III, with the 1,2-dihalogenethanes or the sulfonic acid esters of the 1-hydroxy-2-halogenethanes is effected most suitably under phase transfer catalysis conditions. This reaction is made with stirring in a 2-phase system consisting of water and a water-immiscible organic solvent in the presence of a strong base and a phase-transfer catalyst.

Water-immiscible solvents include suitable organic solvents which show an inert behavior under the reaction conditions, that is, do not interfere with the course of reaction. Suitable solvents are, for example, aliphatic, cycloaliphatic or aromatic hydrocarbons and aromatic halogenated hydrocarbons, such as petroleum ether, benzene, toluene, 1,2-xylene, 1,3-xylene or 1,4-xylene and chlorobenzene. Mixtures of the before-mentioned solvents, too, may be used. In place of the water-immiscible organic solvent it is possible to employ excess 1,2-dihalogenethane. For instance sodium or potassium hydroxide is appropriate to be used as a strong base. The conventional phase transfer catalysts may be used. Catalysts of such type are quaternary ammonium or phosphonium salts, at least one hydrophobic radical with 4 or more carbon atoms being advantageously present in the cation. A radical of this type may be an alkyl radical, aryl or aralkyl radical. Suitable compounds are, for example, tetrabutylammonium hydrogen sulfate, benzyltrimethylammonium chloride and similar compounds. Cations of other known phase transfer catalysts are, for instance, tetrapropylammonium, tetradodecylammonium, benzyltriethylammonium, trihexylmethylammonium, cetyltrimethylammonium, n-alkyltriethylammonium, the alkyl radical carrying 4 or more carbon atoms, e.g. 6 carbon atoms, trioctylmethylammonium, tricaprylmethylammonium (cation of the current product Aliquat 336 commercialized by Messrs. General Mills. Comp., Kankakee, Ill./USA), hexadecyltributylphosphonium. Anions appropriate for these cations are, in particular, hydrogensulfate, chloride and bromide.

Normally, in conducting the reaction, it is unnecessary to warm the reaction mixture. To begin with, a slight temperature rise mostly occurs due to the reaction setting in. At ambient temperature the reaction times are 1 to 40 hours or so, frequently as long as 20 hours. They may be reduced by raising the reaction temperature, for example, up to 60° C.

Based on 1 mole tetrahydrocarbazolone of formula III, normally 1 to 3, preferably 1 to 2, moles of 1,2-dihalogenethane or sulfonic acid ester of the 1-hydroxy-2-halogenethane are employed. If 1,2-dihalogenethane is used not only as reaction component but also as solvent, needless to say, a higher excess of 1,2-dihalogenethane is required. In this case, per mole tetrahydrocarbazolone of the formula III there may be employed for instance up to 15 moles and, if need be, even more, preferably up to 10 moles of 1,2-dihalogenethane. Per mole tetrahydrocarbazolone of the formula III, normally 4 to 15 moles, preferably 5 to 10 moles, of the strong base are employed in the form of an aqueous solution the concentration of which is, as a rule, 10 to 40% by weight, preferably 20 to 40% by weight. Of the catalyst 0.005 to 0.05 mole, preferably 0.005 to 0.02 mole, is required per mole tetrahydrocarbazolone of the formula III. The catalyst as added is, advantageously dissolved in little water. Of course, even larger quantities of the 1,2-dihalogenethane or the sulfonic acid ester of the 1-hydroxy-2-halogenethane, of the strong base and of the catalyst could be employed. Increased quantities, however, are of no advantage. Often it is also possible to reduce the amount of strong base and of catalyst. On doing this, it must, however, be taken into account that while the amount of catalyst is reduced the reaction time is increased. When less than 5 m moles of catalyst are used per 1 mole of compound of formula III, the reaction time is usually uneconomically long.

The new alkyl or arylsulfonic acid esters of the formula IIb, which can also be employed as initial products, are obtained by reacting 1,2,3,4-tetrahydrocarbazol-1-ones of formula III in a very good yield with ethyleneoxide to give the 9-(hydroxyethyl)-1,2,3,4-tetrahydrocarbazol-1-ones of formula IV and, subsequently, converting them in a manner which is in itself known to the alkyl or arylsulfonic acid ester of formula IIb.

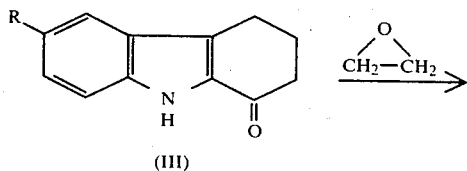

(III)

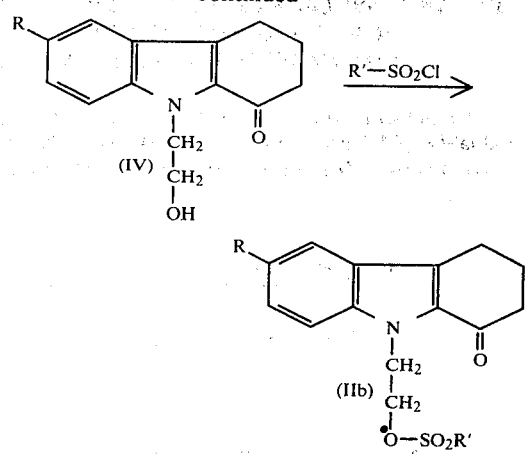

Ethoxylation of the 1,2,3,4-tetrahydrocarbazol-1-ones (formula III) to obtain the 9-hydroxyethyl-1,2,3,4-tetrahydrocarbazol-1-ones (formula IV) is effected in the presence of alkaline catalysts, such as sodium hydroxide, potassium hydroxide and the like in solvents which are inert to the reactants. Dipolar aprotic solvents, such as dimethylformamide and dimethylsulfoxide have proved to be particularly suitable. Further, the presence of water which causes the formation of by-products to be diminished, has turned out to be advantageous.

For converting the 9-hydroxyethyl-1,2,3,4-tetrahydrocarbazol-1-ones of the formula IV to the sulfonic acid esters of the formula IIb practically all of the aromatic or aliphatic sulfonic acid chlorides are suitable. Preferably used is methanesulfochloride. Working is done in indifferent solvents, particularly in hydrocarbons, such as toluene or benzene and in the presence of tertiary bases, such as triethylamine or pyridine.

The 1,2,3,4-tetrahydrocarbazol-1-ones of the formula III, unless already known in the art, are easy to synthesize in accordance with the customary methods for the preparation of 1,2,3,4-tetrahydrocarbazolones. According to the processes known in the art, for example those by Sen and Gosh, Journ. Ind. Chem. Soc. 4 (1927) 477 through 491, and by Coffey, Rec. Trav. Chim. Pay-Bas, 42(1923) 528 through 532, the 2-hydroxymethylenecyclohexanone is synthesized from cyclohexanone and then converted with diazobenzenechloride to the cyclohexane-1,2-dione-monophenyl-hydrazone which turns into the 1,2,3,4-tetrahydrocarbazol-1-one with the action of hot acetic acid. In order to prepare the requisite starting compounds of the formula III the known process merely requires the use of diazobenzenechlorides substituted in the benzene nucleus in the desired way. The desired initial products of the formula III can also be made according to the process of Bloink and Pansacker Soc., 1950, pages 1328 through 1331 from 2-hydroxycyclohexanone with phenylhydrazine being correspondingly substituted in the phenyl nucleus.

The ring closure of 9-halogenethyl-1,2,3,4-tetrahydrocarbazol-1-ones of the formula IIa substituted in the 6-position by alkyl, alkoxy or halogen or of the 9-alkylsulfonyloxyethyl-1,2,3,4-tetrahydrocarbazol-1-one or 9-arylsulfonyloxyethyl-1,2,3,4-tetrahydrocarbazol-1-one of the formula IIb to obtain the formula I compounds of the present invention is effected by ammonia. For this purpose at least 2 moles of ammonia per mole of compound II are theoretically required. However, the carrying-out of the reaction is facilitated if a, e.g., 10- to 70-fold, preferably 20- to 50-fold excess over the theoretically-required quantity of ammonia is used. The ammonia may be employed in the form of a solution in water or in an organic solvent showing an inert behavior under the reaction conditions. Organic solvents suitable for the ammonia are, for instance, alcohols, such as methanol and ethanol. However, liquid ammonia is preferably used. It is advantageous to stir the reaction mixture while cyclisation occurs. It is advantageous, especially with the preferred use of liquid ammonia, to raise the reaction temperature, e.g., as high as 50° to 100° C. In using liquid ammonia, the reaction is conducted in an autoclave.

The compounds of the general formula I according to the present invention and their pharmaceutically acceptable acid addition salts process valuable pharmacological properties. In particular, they exert a strongly-marked psychotropic, more particularly an antidepressive action.

The compounds of the formula I according to the present invention and their pharmaceutically acceptable acid addition salts can be administered to man by themselves, in mixtures one with the other or in pharmaceutical formulations as psychotropic agents, in particular antidepressants which contain as active ingredient at least an effective dose of at least one compound of the formula I according to the present invention or of an acid addition salt thereof in addition to a customary pharmaceutically acceptable carrier substances and carrier additives. Suitable carrier substances are, for example, water, vegetable oils, starch, gelatin, lactose, magnesium stearate, waxes, petroleum jelly and the like. Useful additives include, e.g., wetting agents, explosives, preservatives, etc. The pharmaceutical preparations can be present in a form, such as tablets, capsules, aqueous or oily solutions or suspensions, emulsions, injectable aqueous or oily solutions or suspensions, dispersible powders or aerosol mixtures. In addition to the compounds of the formula I the pharmaceutical preparations may contain one or more of other pharmaceutically active substances, for instance transquilizers, such as diazepam or chlordiazepoxide; cardiovascular agents and vasodilators, such as for example beta-blockers, glyceroltrinitrate, pentaerythritol tetranitrate, molsidomin and carbochromene.

The compounds of the formula I according to the invention are as antidepressants distinctly superior to other known compounds of this kind. Over and above this, they are valuable intermediate products for the manufacture of other likewise pharmacologically active compounds.

The following table gives the pharmacological superiority of the compounds of the present invention over those known compounds having a similar structure and activity.

| Preparation | $LD_{50}$ | Tetrabenazine Dosage Antagonism $ED_{50}$ | $\dfrac{ED_{50}}{ED_{50}}$ |
| --- | --- | --- | --- |
| 8-methyl-2,4,5,6-tetra-hydro-1H-pyrazino[3,2,1-jk] carbazole-hydrochloride Example 1 | 72 | 4 | 18,0 |
| 8-methoxy-2,4,5,6-tetra-hydro-1H-pyrazino[3,2,1-jk] carbazole-hydrochloride Example 2 | 37 | 2 | 18,5 |
| 8-methyl-2,3,3a,4,5,6-hexa-hydro-1H-pyrazino[3,2,1-jk] carbazole-hydrochloride according to German appl. 21 14 230 laid open to first public inspection | 122 | 14 | 8,7 |

The following Working Examples illustrate the preparation of the compounds of the present invention.

In the following examplifications the parts given are parts by weight, the percentages are by weight and the temperatures are degree in Centigrade, unless otherwise noted.

EXAMPLE 1

306 g. (1 mole) of 6-methyl-9-(2-bromoethyl)-1,2,3,4-tetrahydrocarbazol-1-one and 1500 ml. (60 moles) of liquid ammonia are heated to 80° C. in a high-grade steel (vanadium steel 2) autoclave for 20 hours. After evaporation of the excess ammonia the residual crude product is suspended in a mixture consisting of 2000 ml. of ethyl acetate and 1000 ml. of water and sodium hydroxide solution is added until the aqueous layer shows a clear alkaline reaction. The mixture is shaken vigorously, the organic layer is washed with water and dried with sodium sulfate. The hydrochloride of the 8-methyl-2,4,5,6-tetrahydro-1H-pyrazino[3,2,1-jk]carbazole is then deposited by passing in anhydrous hydrogen chloride gas. The resulting hydrochloride is filtered with suction and crystallized from a mixture of ethyl acetate:ethanol (1:1). The recrystallized product melts at 274° to 276° C.

Yield obtained: 87% of the theoretical.
Molecular weight: 260.5.

| $C_{15}H_{16}N_2 \cdot HCl$ | C | H | N | $Cl^{\ominus}$ |
| --- | --- | --- | --- | --- |
| calculated: | 69.2 | 6.5 | 10.7 | 13.6 |
| found: | 68.7 | 6.9 | 10.4 | 13.1 |

In place of the liquid ammonia it is also possible to use solutions of ammonia in organic solvents which under the reaction conditions are chemically indifferent to ammonia or solutions of ammonia in water.

Preparation of the initial product: 6-methyl-9-(2-bromoethyl)-1,2,3,4-tetrahydrocarbazol-1-one:

199 g. (1 mole) of 6-methyl-1,2,3,4-tetrahydrocarbazol-1-one (m.p.: 199° C., as given in literature: 194°–195° C., 195°–196° C., 195° C., cf. Bloink and Pausacker loc. cit. page 1330), 1520 g. (8.1 moles), 1,2-dibromoethane and 1000 ml. (7.5 moles) of aqueous sodium hydroxide solution (30% strength) are taken initially and admixed, while stirring at room temperature, with 4.25 g. (12.5 m mole) of tetrabutylammoniumhydrogensulfate dissolved in 25 ml of water. With a slight temperature rise, the reaction sets in and while continuously stirring, comes to an end after some seven hours' time. For working up, the aqueous alkaline layer is separated, the organic layer washed with water and the excess dibromoethane distilled off in vacuo. The residue is recrystallized from 200 ml. of ethanol. 281 g. (92% of the theoretical) of 6-methyl-9-(2-ethylbromide)-1,2,3,4-tetrahydrocarbazol-1-one (melting at 103° C.). The amount of the tetrabutylammoniumhydrogensulfate used as catalyst can be reduced to 5 m moles per 1 mole of the carbazolone employed, but the reaction takes twice as long when this change is made.

In lieu, of the excess dibromoethane it is possible to use other solvents, for example toluene, benzene or chlorobenzene, which are imiscible in water and inactive under the conditions of the reaction.

199 g. (1 mole) of 6-methyl-1,2,3,4-tetrahydrocarbazol-1-one and 376 g. (2 moles) of 1,2-dibromoethane are dissolved in 1000 ml. of toluene and stirred together with 1000 ml. of sodium hydroxide solution and 4.25 g. (12.5 m moles) of tetrabutylammoniumhydrogensulfate for 10 hours at 60° C. After evaporating the aqueous layer, distilling off the solvent and recrystallizing the residual crude product, 275 g. of 6-methyl-9-(2-bromoethyl)-1,2,3,4-tetrahydrocarbazol-1-one (90% of the theoretical) melting at 102° to 103° C. are obtained.

| $C_{15}H_{16}BrNO$ (having a molecular weight of 306) | | | | | |
|---|---|---|---|---|---|
| | C | H | Br | N | O |
| calculated: | 58.8 | 5.2 | 26.1 | 4.6 | 5.2 |
| found: | 59.0 | 5.4 | 25.5 | 4.6 | 5.6 |

In place of the 6-methyl-9-(2-bromoethyl)-1,2,3,4-tetrahydrocarbazol-1-one it is also possible to employ the corresponding ethyl chloride derivative which is obtained by the following route:

100 g. (0.5 mole) of 6-methyl-1,2,3,4-tetrahydrocarbazol-1-one and 500 ml. (4 mole) of ethylene chloride are stirred together with 500 ml. of aqueous sodium hydroxide solution (30% strength) and 4.25 g. (12.5 m moles) of tetrabutylammoniumhydrogen sulfate for 20 hours at 20° to 30° C. Working up is done according to the procedure given in Example 1. 112 g. (=86% of the theoretical) of 6-methyl-9-(2-chloroethyl)-1,2,3,4-tetrahydrocarbazol-1-one (melting at 108° C.) are thus obtained.

| $C_{15}H_{16}ClNO$ (having a molecular weight of 261.5) | | | | | |
|---|---|---|---|---|---|
| | C | H | Cl | N | O |
| calculated: | 38;9 | 6.1 | 13.6 | 5.4 | 6.1 |
| found: | 69;4 | 6.1 | 13.1 | 5;5 | 6.3 |

Instead of the 1,2-dihalogenethane it is also possible to use the sulfonic acid ester of the 1-hydroxy-2-halogenethanes as initial products which are obtained in the following manner:

100 g. (0.5 mole) of 6-methyl-1,2,3,4-tetrahydrocarbazol-1-one and 234.5 g. (1 mole) of p-toluenesulfonic acid-β-chloroethylester are dissolved in 700 ml. of toluene and stirred together with a solution of 4.25 g. (12.5 m moles) of tetrabutylammoniumhydrogensulfate in 500 ml. of aqueous sodium hydroxide solution (30% strength) for 10 hours at room temperature. The organic layer is separated, washed with water and concentrated by evaporation. 108 g. (=83% of the theoretical) of 6-methyl-9-(2-chloroethyl)-1,2,3,4-tetrahydrocarbazol-1-one (melting at 106° to 107° C.) are thus obtained.

EXAMPLE 2

6-Methoxy-9-(2-bromoethyl)-1,2,3,4-tetrahydrocarbazol-1-one are reacted according to the instructions given in Example 1 to obtain 8-methoxy-2,4,5,6-tetrahydro-1H-pyrazino[3,2,1-jk] carbazole-hydrochlorides which melt at 288° C.

Yield obtained: 86% of the theoretical.
Molecular weight: 276.5.

| $C_{15}H_{16}N_2O \cdot HCl$ | | | | | |
|---|---|---|---|---|---|
| | C | H | O | N | $Cl^\ominus$ |
| calculated: | 65.2 | 6.1 | 5.8 | 10.0 | 12.9 |
| found: | 65.3 | 6.1 | 5.7 | 10.2 | 12.8 |

Preparation of the initial products:

(a) 6-methoxy-1,2,3,4-tetrahydrocarbazol-1-one 123 g. (1 mole) of p-methoxyaniline are dissolved in 600 ml. of water with the addition of 260 g. of concentrated hydrochloric acid. After cooling down to 0° C., 69 g. of sodium nitrite dissolved in 130 ml. of water are added dropwise to the solution. The diazotation being complete, 350 ml. of methanol and 148 g. (1 mole) of the sodium salt of the 1-hydroxymethylene-cyclohexanone are added and the temperature is maintained below +3° C. by adding ice. By the addition of 33.5 g. of anhydrous sodium carbonate and 250 g. of crystallized sodium acetate the solution is standardized to pH 5 to 6. After coupling is completed (10 to 12 hours or so), the solution is made up to a pH 9 to 9.5, stirred three hours at room temperature, filtered with suction and washed with water until free from alkali. Thus, cyclohexanedione-mono-(p-methoxyphenyl) hydrazone (which melts at 177° C.) is obtained at a yield of 202 g. (=87% of the theoretical).

| | C | H | N | O |
|---|---|---|---|---|
| calculated: | 67.2 | 6.9 | 12.1 | 13.8 |
| found: | 67.1 | 6.7 | 11.9 | 13.9 |

232 g. (1 mole) of cyclohexanedione-mono-(p-methoxy)phenyl-hydrazone, 1200 ml. of water, 350 g. of sulfuric acid (65 Be) and 100 ml. of ethanol are allowed to boil under reflux for three hours. After cooling down, the mixture is filtered with suction and rendered free from acid by washing with water. The resultant 6-methoxy-1,2,3,4-tetrahydrocarbazol-1-one melts at 222° C. and gives a yield of 193 g. (=90% of the theoretical).

| | C | H | N | O |
|---|---|---|---|---|
| calculated: | 72.6 | 6.0 | 14.9 | 6.5 |
| found: | 72.1 | 5.9 | 14.3 | 6.6 |

According to the foregoing instructions one can prepare other 1,2,3,4-tetrahydrocarbazol-1-ones substituted in the 6-position by the use of differently substituted anilines. The Bloink and Pausacker literature reference loc. cit., page 1330 indicates a melting point of 180° to 182° for the 6-methoxy-1,2,3,4-tetrahydrocarbazol-1-one, in which case, however, the compound described by the named authors still contains 5 moles of crystal benzene.

(b) 6-methoxy-9-(2-bromoethyl)-1,2,3,4-tetrahydrocarbazol-1-one 215 g. (1 mole) of 6-methoxy-1,2,3,4-tetrahydrocarbazol-1-one (m.p.: 222° C.), 1500 g. of 1,2-dibromoethane, 1000 ml. of aqueous sodium hydroxide solution (30% strength) and 2. g. of tetrabutylammoniumhydrogensulfate are stirred at room temperature for 20 hours and, as stated in Example 1, worked up. 286 g. (=89% of the theoretical) of 6-methoxy-9-(2-bromoethyl)-1,2,3,4-tetrahydrocarbazol-1-one (having a melting point of 119° C.) are thus obtained.

| $C_{15}H_{16}BrNO$: Molecular weight of 322 | | | | |
|---|---|---|---|---|
| | C | H | Br | N | O |
| calculated: | 55.9 | 5.0 | 24.8 | 4.3 | 9.9 |
| found: | 56.1 | 5.0 | 24.5 | 4.5 | 9.5 |

EXAMPLE 3

6-chloro-9-(2-bromoethyl)-1,2,3,4-tetrahydrocarbazol-1-one is reacted according to the instructions of Example 1 and 8-chloro-2,4,5,6-tetrahydro-1H-pyrazino[3,2,1-jk] carbazole-hydrochloride (which melts at 295° to 305° C.) is thus obtained.
Yield obtained: 90% of the theoretical.
Molecular weight: 231.

| $C_{14}H_{13}ClN_2 \cdot HCl$ | | | | |
|---|---|---|---|---|
| | C | H | N | Cl | $Cl^{\ominus}$ |
| calculated: | 59.8 | 5.0 | 10.0 | 25.2 | 12,6 |
| found: | 59.8 | 5.1 | 9.6 | 24.6 | 11.9 |

The reactant 6-chloro-9-(2-ethyl bromide)-1,2,3,4-tetrahydrocarbazol-1-one is obtained by reaction of 6-chloro-1,2,3,4-tetrahydrocarbazol-1-one (m.p.: 226° C.) in accordance with the instructions of Example 1 concerning the preparation of the initial products. 6-chloro-9-(2-bromoethyl)-1,2,3,4-tetrahydrocarbazol-1-one, which melts at 121° C., is obtained with a yield of 86% of the theoretical and has a molecular weight of 326.5.

| $C_{14}H_{13}BrClNO$ | | | | | |
|---|---|---|---|---|---|
| | C | H | Br | Cl | N | O |
| calculated: | 51.5 | 4.0 | 24.4 | 10.9 | 4.3 | 4.9 |
| found: | 51.9 | 4.0 | 23.9 | 11.2 | 4.3 | 5.3 |

EXAMPLE 4

6-bromo-9-(2-bromoethyl)-1,2,3,4-tetrahydrocarbazol-1-one is reacted in accordance with the instructions of Example 1 and
8-bromo-2,4,5,6-tetrahydro-1H-pyrazino [3,2,1-jk]carbazolehydrochloride which melts at 298° to 300° C., is thus obtained at a yield of 85% of the theoretical and with a molecular weight of 325.5.

| $C_{14}H_{13}BrN_2 \cdot HCl$ | | | | |
|---|---|---|---|---|
| | C | H | N | Br | $Cl^{\ominus}$ |
| calculated: | 51.8 | 4.3 | 8.6 | 24.6 | 10.9 |
| found: | 51.7 | 4.3 | 8.4 | 24.2 | 10.1 |

The 6-fluoro-9-(2-bromoethyl)-1,2,3,4-tetrahydrocarbazol-1-one used as reactant is obtained from 6-bromo-1,2,3,4-tetrahydrocarbazol-1-one (m.p.: 227° C.) in accordance with the instructions of Example 1 regarding the preparation of the initial products; it melts at 126° C., is obtained at a yield of 88% of the theoretical and has a molecular weight of 371.

| $C_{14}H_{13}Br_2NO$ | | | | |
|---|---|---|---|---|
| | C | H | Br | N | O |
| calculated: | 45.2 | 3.5 | 43.1 | 3.8 | 4.3 |
| found: | 45.0 | 3.4 | 42.8 | 3.6 | 4.5 |

EXAMPLE 5

6-fluoro-9-(2-bromoethyl)-1,2,3,4-tetrahydrocarbazol-1-one is reacted in accordance with the instructions of Example 1 to obtain 8-fluoro-2,4,5,6-tetrahydro-1H pyrazino [3,2,1-jk]carbazole hydrochloride which melts at 303° to 305° C., at a yield of 81% of the theoretical and with a molecular weight of 264.5.

| $C_{14}H_{13}FN_2 \cdot HCl$ | | | | |
|---|---|---|---|---|
| | Cl | H | F | N | $Cl^{\ominus}$ |
| calculated: | 63.5 | 5.3 | 7.2 | 10.6 | 13.4 |
| found: | 62.8 | 5.5 | 6.8 | 10.3 | 13.9 |

The 6-fluoro-9-(2-bromoethyl)-1,2,3,4-tetrahydrocarbazol-1-one used as reactant is obtained from 6-fluoro-1,2,3,4-tetrahydrocarbazol-1-one (m.p. 210°) in accordance with the instructions of Example 1 regarding the preparation of the initial products; it melts at 131°, is obtained at a yield of 76% of the theoretical and with a molecular weight of 310.

| $C_{14}H_{13}BrFNO$ | | | | |
|---|---|---|---|---|
| | C | H | Br | F | N |
| calculated: | 54.2 | 4.2 | 25.8 | 6.1 | 4.5 |
| found: | 54.1 | 4.1 | 25.8 | 5.9 | 4.9 |

EXAMPLE 6

122 g. (0.38 mole) of 6-methyl-9-($\beta$-methyl-sulfonyloxy-ethyl)-1,2,3,4-tetrahydrocarbazol-1-one admixed with 650 ml. (26 moles) of liquid ammonia are heated in an autoclave at 50° C. for 20 hours. The residue remaining after evaporation of the ammonia is suspended in a mixture of 1000 ml. of ethyl acetate and 500 ml. of water and diluted sodium hydroxide solution is added until the aqueous layer shows a distinct alkaline reaction. The whole is shaken thoroughly, the organic layer is washed with water and dried with sodium sulfate; and the hydrochloride of the 8-methyl-2,4,5,6-tetrahydro-1H-pyrazino[3,2,1-jk] carbazole is deposited by passing in anhydrous hydrogen chloride gas. The reaction product is filtered with suction and recrystallized from a mixture of ethyl acetate:ethanol (1:1). The recrystallized product melts at 274° to 276°; yield obtained: 79.2 g. (=80% of the theoretical).
$C_{15}H_{16}N_2$-HCl Molecular weight: 260.5.
Preparation of the initial products:
6-methyl-9-(2-hydroxyethyl)-1,2,3,4-tetrahydrocarbazol-1-one:
199 g. (1mole) of 6-methyl-1,2,3,4-tetrahydrocarbazol-1-one dissolved in 2000 ml. of dimethylformamide are taken initially and 5.6 g. (0.1 mole) of potassium chloride dissolved in 200 ml. of water are added. Thereafter 66.1 g.=74.2 ml. (1.5 mole) of ethyleneoxide are added at room temperature and heated up to 50° C. within 30 minutes, a maximum pressure of 0.2 to 0.5 bar being generated. Stirring is done for 20 hours at 50° C., the solvent is distilled off in a vacuum and, the residue is stirred with a mixture of 800 ml. water and 10 ml. of glacial acetic acid; the product (which takes a crystalline form) is filtered with suction, washed with 500 ml. water and dried at 40° C. in vacuo.

Yield obtained: 239.5 g. (98.6% of the theoretical).
Melting point: 113° to 116° C.
$C_{15}H_{17}NO_2$ Molecular weight: 243.

6-methyl-9-(β-metholsulfonyloxyethyl)-1,2,3,4-tetrahydrocarbazol-1-one:

239.5 g. (0.98 mole) of 6-methyl-9-(2-hydroxyethyl)-1,2,3,4-tetrahydrocarbazol-1-one are dissolved in 2000 ml. of toluene admixed with 109.6 g. (1.08 mole) of triethylamine and 124.3 g. (1.08 mole) of methanesulfochloride are added dropwise within 15 minutes. The temperature is maintained at 25° to 30° C. by cooling. Subsequently, the mixture is stirred for 30 minutes while the temperature decreases. After the addition of 3000 ml. of toluene, 500 ml. water and 15 ml. of concentrated hydrochloric acid, the whole is heated as high as 55° C. The toluene phase is separated, washed with 500 ml. water and concentrated by evaporation. The residue is recrystallized from 5 l. of isopropanol.

Yield obtained: 280 g. (89% of the theoretical).
Melting poing: 131° to 133° C. with decomposition.
$C_6H_{19}NO_4S$ Molecular weight: 321.

What we claim is:

1. A 2,4,5,6-tetrahydro-1H-pyrazino[3,2,1-jk]carbazole substituted in the 8-position and having the formula

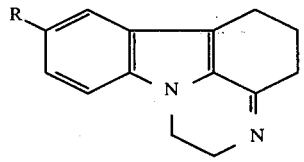

(I)

wherein R represents an alkyl or alkoxy group having 1 to 4 carbon atoms or a fluorine, chlorine or bromine atom, or a pharmaceutically-acceptable acid-addition salt thereof.

2. A compound as set forth in claim 1 or a pharmaceutically-acceptable acid-addition salt thereof wherein R stands for a methyl or methoxy group.

3. A process for producing a compound, as set forth in claim 1, which comprises (a) reacting with ammonia a 6,9-disubstituted 1,2,3,4-tetrahydrocarbazol-1-one of the formula

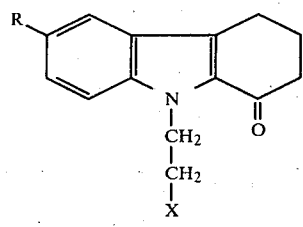

(II), wherein R has the meaning set forth in claim 1 and X denotes a bromine, chlorine or iodine atom, and (b) cyclising the resulting product.

4. A process as set forth in claim 3 wherein the ammonia is liquid ammonia.

5. A process as set forth in claim 3 or 4 which comprises conducting the reaction within the temperature range of from 50° to 100° C. with stirring.

6. An antidepressant composition having an effective amount of a compound as set forth in claim 1 or 2 in combination with pharmaceutically-acceptable carrier.

7. 8-methyl-2,4,5,6-tetrahydro-1H-pyrazino[3,2,1-jk]-carbazole or a pharmaceutically-acceptable acid-addition salt thereof.

8. 8-methoxy-2,4,5,6-tetrahydro-1H-pyrazino[3,2,1-jk]-carbazole or a pharmaceutically-acceptable acid-addition salt thereof.

9. A 6,9-disubstituted 1,2,3,4-tetrahydrocarbazol-1-one of the formula

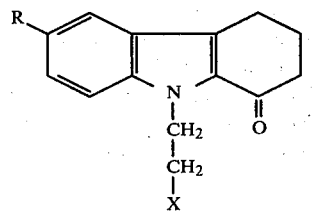

(II)

wherein
R represents an alkyl or alkoxy group having 1 to 4 carbon atoms, a fluorine, chlorine or bromine atom and
X means a chlorine, bromine or iodine atom.

10. A 6,9-disubstituted 1,2,3,4-tetra-hydrocarbazol-1-one as set forth in claim 9 wherein R denotes methyl, and X represents a chlorine or bromine atom.

11. A 6,9-disubstituted 1,2,3,4-tetra-hydrocarbazol-1-one as set forth in claim 9 wherein R denotes methoxy, and X represents a chlorine or bromine atom.

* * * * *